(12) United States Patent
Autefage et al.

(10) Patent No.: US 8,216,630 B2
(45) Date of Patent: Jul. 10, 2012

(54) POROUS BIOMATERIALS SURFACE ACTIVATION METHOD

(75) Inventors: Hélène Autefage, Toulouse (FR); Sophie Cazalbou, Rebigue (FR); Christèle Combes, Ramonville St Agne (FR); Christian Rey, Aureville (FR)

(73) Assignees: Institut National Polytechnique de Toulouse, Toulouse Cedex (FR); TEKNIMED, Vic-En-Bigorre Cedex (FR)

( * ) Notice: Subject to any disclaimer, the term of this patent is extended or adjusted under 35 U.S.C. 154(b) by 218 days.

(21) Appl. No.: 12/487,101

(22) Filed: Jun. 18, 2009

(65) Prior Publication Data

US 2010/0323094 A1     Dec. 23, 2010

(51) Int. Cl.
*B05D 3/02*        (2006.01)
*A61L 27/32*       (2006.01)
*A61F 2/28*        (2006.01)
*A61K 33/42*       (2006.01)
(52) U.S. Cl. ...... 427/2.1; 427/2.24; 427/2.27; 427/2.29; 427/372.2; 424/422; 424/423; 424/602
(58) Field of Classification Search .................. 427/2.1, 427/2.24–2.29; 424/422, 423, 602
See application file for complete search history.

(56) References Cited

FOREIGN PATENT DOCUMENTS

| EP | 0437975 A1 | 7/1991 |
|---|---|---|
| EP | 437975 A1 * | 7/1991 |
| EP | 1384524 A2 | 1/2004 |
| FR | 2842750 A1 * | 1/2004 |

* cited by examiner

*Primary Examiner* — Timothy Meeks
*Assistant Examiner* — Cachet Sellman
(74) *Attorney, Agent, or Firm* — Birch, Stewart, Kolasch & Birch, LLP

(57) ABSTRACT

The present invention relates to a porous biomaterials surface activation method by coating with a layer of apatitic nanocrystals in order to increase their surface reactivity. The method according to the invention is characterized by the following steps: a) preparing a nanocrystalline apatitic calcium phosphate analogous to bone mineral by mixing a calcium salt solution with a phosphate salt solution in a Ca/P ratio ranging between 1.3 and 2 at a temperature ranging between 0 and 60 ° C., b) slurrying the mixture obtained in step a) in an aqueous solution so as to obtain a fluid, homogeneous paste containing 80 to 98% of water, c) bringing a porous biomaterial into contact with the suspension obtained in step b), d) drying the porous biomaterial at a temperature below 100 ° C.

21 Claims, 3 Drawing Sheets

POROUS BIOMATERIALS SURFACE ACTIVATION METHOD

FIELD OF THE INVENTION

The present invention relates to the field of ceramic implants and orthopedic prostheses. More specifically, it relates to a porous biomaterials surface activation method by coating with a layer of apatitic nanocrystals in order to increase their surface reactivity.

BACKGROUND OF THE INVENTION

Phosphocalcic ceramics first appeared in the field of biomaterials around twenty years ago. They make it possible to offset the drawbacks of biologic grafts (autografts (also known as autogenous or autologous grafts), allografts (also known as allogenic or homologous grafts) and xenografts) while promoting bone reconstructing. Indeed autografts require a second surgical operation on the donor site; they only enable, in general, the filling of small volumes due to the little amount of tissue available, said tissue sometimes being of poor quality particularly in elderly patients, and they are associated with a certain morbidity rate. Allografting leads to an often reduced re-colonization [Enneking W. F., Journal of bone and joint surgery, 73-A, 8, 1123-1141, 1991] and infection risks that can be responsible for massive osteolyses encountered in some patients.

Consequently, synthetic ceramics are commonly used by surgeons (orthopedic, maxillofacial, plastic or dental), since a loss of bone substance requires filling.

Hydroxyapatite (HA) and tricalcic phosphate (TCP) are the two most widely used calcium phosphates in the field of biomaterials [Li Shihong, De Groot Klaas, Layrolle Pierre, Van Blitterswijk Clamens, De Wijn Joost; Porous ceramic body, U.S. Pat. No. 6,479,418, 2002], even though these two phases have very different physical-chemical properties.

Hydroxyapatite may be considered as one of the least soluble calcium phosphates and it is a non-bioresorbable biomaterial. Consequently, hydroxyapatite is commonly used for coating metal prostheses so as to enhance the biointegration of the material. TCP, which for its part is much more soluble, makes up a resorbable material that is progressively replaced by bone. However, its resorption rate cannot be modulated ("Bioceramics and their clinical applications", Ed. T. Kokubo, CRC Press, 2008).

Biphasic ceramics made up of a variable mixture of HA and TCP enable the bioresorbability to be modulated as a function of the level of TCP used and for this reason they have enjoyed considerable success in the field of biomaterials ("Bioceramics and their clinical applications", Ed. T. Kokubo, CRC Press, 2008).

All of these ceramics are obtained by sintering at high temperature and the biological activity of such type of material is limited on account of the low specific surface of the sintered materials and their weak interaction with the various proteins and growth factors responsible for adhesion, proliferation and cell expression. They are moreover quite far removed from bone mineral and behave differently, both in chemical and biological terms.

Most known nanocrystalline apatite deposition procedures make use of supersaturated calcium phosphate solutions that are difficult to use industrially, with processing times sometimes lasting several days. The most widely employed method consists in using SBF (Simulated Body Fluid) (Kokubo T, Takadama H (2006), How useful is SBF in predicting in vivo bone bioactivity, Biomaterials 27, 2907-2915).

Other methods, on the same principle, have been developed using more concentrated solutions (Layrolle P, Stigter M, De Groot K, Liu Y, Method for applying a bioactive coating on a medical device, 2006, U.S. Pat. No. 6,994,883 and Layrolle P, de Groot K, de Bruijn J, van Blitterswijk C, Huipin Y, Method for coating medical implants, 2004, U.S. Pat. No. 6,733,503, continuation of 2001, U.S. Pat. No. 6,207,218; and also Li P, Wen H B, Hippensteel E, Biological agent-containing ceramic coating and method, 2006, U.S. Pat. No. 7,087,086, and Li P, Bioactive ceramic coating and method, 2003, U.S. Pat. No. 6,569,589). These methods have moreover been rarely used to coat the inside of ceramic pores.

Simple and rapid methods enabling a biological activation of the surface of sintered porous ceramics thus do not exist. The aforementioned patents have not as yet been applied industrially. Moreover, the apatites obtained by these methods are generally mature and have a lower reactivity than those precipitated and deposited by the present method, which offers the possibility of choosing the maturation time.

SUMMARY OF THE INVENTION

The present invention aims at resolving the drawbacks of the prior art by proposing a method that makes it possible to deposit, at low temperature on biomaterials with interconnected porosity, a resorbable bioactive mineral phase, of various thickness, comprised of calcium phosphate nanocrystals analogous to bone mineral. The method according to the invention comprises an impregnation of the porous material by a suspension of bioactive calcium phosphate followed by drying under precise conditions.

This method enables the deposition of very reactive nanocrystals that considerably increase the surface reactivity of ceramics and enable the adsorption of bioactive substances capable of orienting cell activity. The main advantage of this method is to activate the surface of low specific surface and not very reactive sintered materials.

The method according to the invention is based on the surface properties of nanocrystals and their ability to fix on certain surfaces, particularly those of porous phosphocalcic ceramics. This method is simple and efficient and it does not entail any delicate or costly manipulation. As explained hereafter, the gels may be obtained by the double decomposition method commonly used in industry. Their composition and their viscosity may be perfectly known and controlled. Thus, the characteristics of the gel (and consequently of the deposition) are perfectly adapted to the characteristics of the material to be treated. The method provides a deposit of nanocrystalline apatites enabling a biological activation, either in an intrinsic manner or through the use of bioactive mineral ions, active molecules or both.

The invention thus proposes a method enabling an activation of the surface of these ceramics by a deposition of apatitic calcium phosphate analogous to bone mineral. This deposit of very high specific surface (up to 300 m$^2$/g) allows to increase the surface reactivity of the material and facilitates the adsorption of bioactive substances capable of orienting cell activity. This surface treatment method enables the entire surface of the ceramic to be coated, including in particular the internal surfaces of the interconnected pores of the material.

The mineral phase deposited is made of nanocrystals analogous to those that constitute bone mineral. These are characterized by the presence, at the surface, of a labile, highly reactive hydrated layer constituted of easily and rapidly mobilizable ions [Cazalbou S., "*Echanges cationiques impliquant des apatites nanocristallines analogues au minéral osseux*" (Cationic exchanges involving nanocrystalline apatites analogous to bone mineral), INPT Thesis, Toulouse 2000]. These ions are capable of participating in numerous ion exchange reactions and some may have, if necessary, a biological activity. This hydrated layer moreover facilitates a better interaction with the organic molecules of the living being (proteins, growth factors, etc.) [Midy V., Rey C., Bres E., Dard M., Basic fibroblast growth factor adsorption and release of calcium phosphate, Journal of Biomed. and Mat. Res., 405-411, 1998]. Such labile environments seem to confer on the bone crystals all their surface reactivity. They are found in large quantities in the bone mineral, in greater quantity in young bones than in more mature bones [Boivin, G; Deloffre, P; Perrat, B; Panczer, G; Boudeulle, M; Mauras, Y; Allain, P; Tsouderos, Y; Meunier, P J; Strontium distribution and interactions with bone mineral in monkey iliac bone after strontium salt (S 12911) administration, J. Bone and Min. Res. 11, 9, 1302-1311, 1996]. In addition, the similarity between the deposited phase and the bone mineral both with regard to the chemical composition and the crystalline morphology is liable to promote perfect biointegration.

Another advantage of the method resides in the possibility of incorporating in the apatite, either at the time of its formation or after its formation, bioactive mineral ions such as strontium, magnesium, manganese, vanadate ions, etc., which can remain mobilizable and active when they are incorporated in the hydrated layer.

Similarly, the association of proteins or growth factors promoting osteogenesis or vascularization may be carried out during the coating process or instead after deposition of the nanocrystalline apatitic layer. The combination of phosphocalcic ceramics with growth factors such as Bone Morphogenetic Proteins (BMP), for example, imparts osteoinductive properties to the material [Yuan, H; Zou, P; Yang, Z; Ahang, X; De Bruijin, J D; De Groot, K; Bone morphogenetic protein and ceramic-induced osteogenesis, J. Mater. Sci. Mater. Med.; 9, 12, 717-21; 1998] and thus facilitates bone cicatrisation. The nanocrystalline apatite coating allows to improve the adsorption properties of the material vis-á-vis such proteins.

The combination of bioactive substances with ceramics becomes possible after deposition of the nanocrystalline apatitic layer (ions, proteins, growth factors, growth hormones, etc.). It is then possible to act on the biological behavior of the material. It is in this sense that the method may be described as a surface activation of ceramics.

It is moreover anticipated that the enhanced properties of the nanocrystalline apatite coating with regard to the adsorption of proteins and ion exchanges may facilitate associations, directly at the surgical site, with biologically active circulating factors.

DETAILED DESCRIPTION OF THE INVENTION

Figure 1:
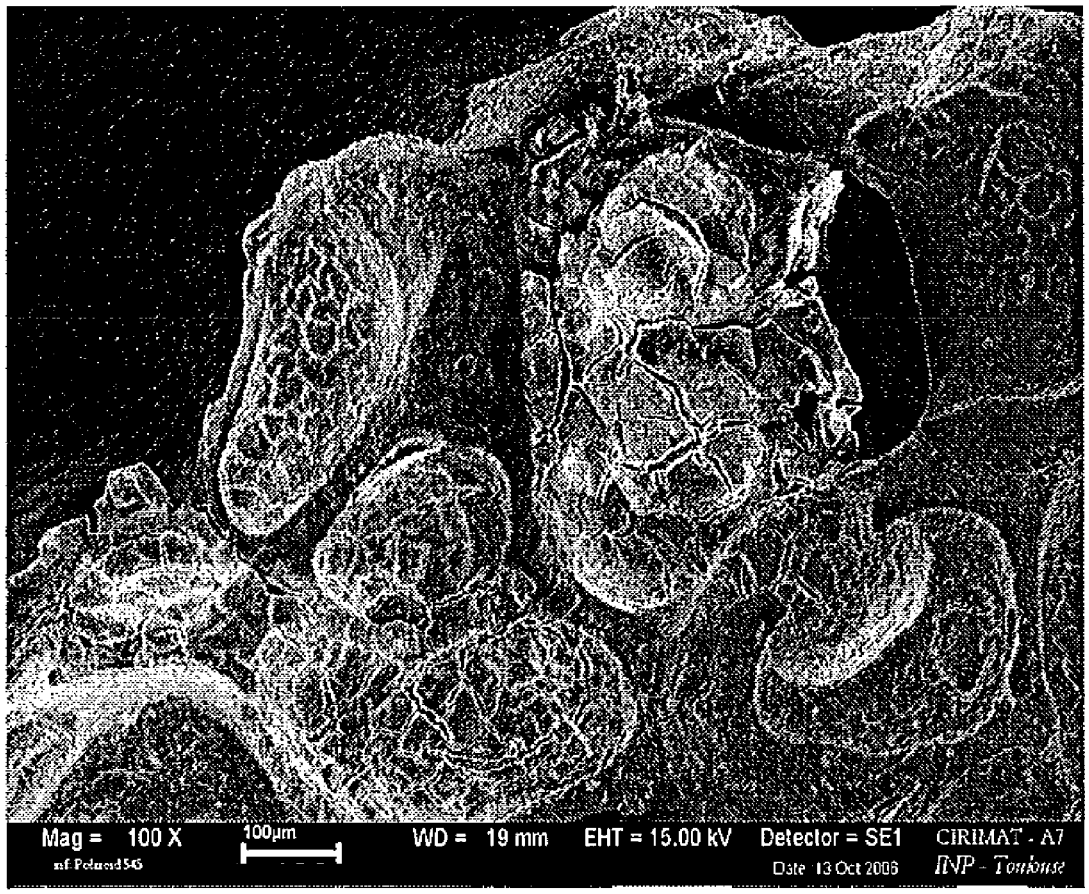
FIG. 1 shows a micrograph of a nanocrystalline apatite layer deposited inside the pores of a biphasic HA-TCP ceramic, in accordance with the present invention.

More specifically, the present invention relates to a porous biomaterials surface activation method, wherein it comprises the following steps:

a) preparing a nanocrystalline apatitic calcium phosphate analogous to bone mineral by mixing a calcium salt solution with a phosphate salt solution in a Ca/P ratio ranging between 1.3 and 2, at a temperature ranging between 0 and 60° C., b) slurrying the mixture obtained in step a) in an aqueous solution so as to obtain a homogeneous, fluid paste containing 80 to 98% of water, c) contacting a porous biomaterial with the suspension obtained in step b), d) drying the porous biomaterial at a temperature below 100° C.

The nanocrystalline phase of calcium phosphate analogous to bone mineral is obtained by double decomposition between a calcium salt solution (which may if necessary contain other ions, in particular biologically active ions) and a phosphate salt and a carbonate salt solution (which may if necessary contain other ions, in particular biologically active ions). The main advantage of this synthesis method resides in the fact that the pH remains constant, the synthesis solution being buffered by an excess of phosphate salt. In addition, this method avoids the occurrence of foreign phases during the precipitation and limits dissolution-precipitation phenomena. It has an excellent reproducibility. The precipitate obtained is washed and recovered by filtration.

The nanocrystalline apatitic calcium phosphate thereby obtained has a controlled surface reactivity. Indeed it has a surface hydrated layer comprising mobile ions, the extent and the composition of which are controlled by the maturation of the nanocrystals in the precipitation solution and/or the presence of additives ($Mg^{2+}$, $CO_3^{2-}$, $P_2O_7^{4-}$) in said precipitation solution.

In a specific embodiment of the method object of the invention, the mixture obtained once step a) is completed undergoes a treatment step to modify the surface of the nanocrystals during which it is brought into contact with at least one compound exhibiting a biological activity and/or modifying the surface properties of the nanocrystals, said compound being selected from mineral ions or organic molecules or a mixture thereof. The surface treatment may also be carried out once step d) is completed, cumulatively with step a) or in an exclusive manner.

During this surface treatment step, the precipitate of nanocrystals may thus exhibit surface properties defined by the addition either of mineral ions or organic molecules, or a combination thereof.

The wet precipitate obtained may thus be subjected to an ion exchange through contact for several minutes with an aqueous solution containing ions exhibiting a biological activity and/or modifying the surface properties of the nanocrystals—such as for example $Mg^{2+}$, $Sr^{2+}$, $Mn^{2+}$, $SiO_4^{4-}$, $VO_4^{3-}$ ions. The modified precipitate obtained is washed and filtered out.

It is also possible at the end of step a) to associate the precipitate with biologically active molecules and/or which modify the surface properties of nanocrystals, by adsorption of said nanocrystals on the very reactive mineral surface, such as for example growth factors, antibiotics, etc.

During step b), the precipitate is suspended (slurried up) in an aqueous solution so as to obtain a fluid paste containing between 80% and 98% of water. The density of the suspension directly determines the thickness of the deposit.

Preferably, the mixture obtained at the end of step a) has a Ca/P ratio ranging between 1.33 and 1.67, which improves the biointegration properties as well as the reactivity of the porous material.

In a specific embodiment of the invention, before it is brought into contact with the nanocrystalline apatite gel, the porous biomaterial may be cleared of any impurity or any organic pollutants that could hinder the wettability of the porous surface by the aqueous suspension, for example by prior calcination/heating for several minutes (from 3 to 5 minutes) in air, at a temperature close to 900° C., or instead by a UV-ozonization treatment, or any other treatment enabling the elimination of surface organic pollutants.

The porous material to be treated is then contacted with the suspension. This step may be carried out by immersion of the biomaterial in the solution obtained in step b) or instead spraying or coating the solution obtained in step b) on the biomaterial. The penetration of the deposit may be facilitated by placing the whole under partial vacuum, typically between 10 to 30 mm Hg; the air occluded in the pores is eliminated and replaced by the suspension. This procedure may be repeated.

The material is then dried at a temperature not exceeding 100° C. and preferably at low temperature in a ventilated oven or under partial vacuum.

During this drying phase, the nanocrystals are deposited on the walls of the pores and form a coating. Cracks may nevertheless appear within this coating. In order to obtain a more even and more adherent deposit, it is possible to include in the method a step enabling the thickening of the gel by dehydration. This partial and progressive dehydration may be carried out in various ways, for example by controlling the partial water vapor pressure in the gas phase in contact with the material or by using a solvent, for example ethanol. The material, after impregnation, is introduced for example in a sealed enclosure in the presence of ethanol vapor at a temperature close to 60° C. for at least 24 hours then recovered and dried as previously. This step has an influence on the maturation of the nanocrystals as well as on the morphology of the coating, which appear more homogeneous with fewer cracks.

The surfaces thereby prepared can adsorb active ingredients, particularly growth factors, antibiotics and drugs, making it possible to control bone diseases (osteoporosis for example). The adsorption is achieved by contact between the "activated" ceramic and the solution containing the active ingredient. This method of association may be superimposed on or replace the surface treatment of the nanocrystals carried out at the end of step a).

Steps b), c), and d) may be repeated if necessary. The characteristics of the gel and/or the number of treatments make it possible to obtain various deposition thicknesses, typically of some 1 to 10 μm.

A modulated repetition, i.e. carried out by modifying the surface treatment, also makes it possible to obtain successive deposits exhibiting complementary biological properties, for example a deposition facilitating the recruitment and the growth of osteoblastic cells that build up the bone and containing strontium ions, followed by a deposition favoring vascularization and containing the growth factor VEGF. These successive "onionskin" depositions make is possible to control and promote tissue repair processes (vascularization of the implant, then its re-colonization by bone tissue). The thicknesses are nevertheless limited by the necessity not to significantly alter or clog the pores of the material.

A method according to the invention thus comprises the formation of a nanocrystalline apatite layer by impregnation with a gel. The principal advantage of this method is to provide a biological activation to sintered materials based on calcium phosphate in a simple manner and at low cost.

Advantageously and according to the invention, it is possible to vary the thickness of the deposit by a control of the viscosity of the gel used during the treatment.

Advantageously and according to the invention, the specific surface of the treated material, and its surface reactivity, may be considerably increased by a control of the physicochemical properties of the crystals constituting the gel (particularly the maturation, or the surface modifications).

Advantageously and according to the invention, the morphology of the deposit as well as its surface state may be modified.

Advantageously and according to the invention, the method of drying makes it possible to improve the adhesion of the coating to the substrate.

The method thus disclosed according to the present invention is different from that disclosed in French patent FR 2 842 750 "Procédé permettant de recouvrir à basse température des surfaces par des phosphates apatitics nanocrystallines, à partir d'une suspension aqueuse de phosphate amorphe" ("Low temperature process for coating surfaces with nanocrystalline apatite phosphates from an aqueous suspension of amorphous phosphate") in several ways:

(i) The method according to the invention saves having to use an intermediary, viz. the amorphous phosphate, to achieve a nanocrystalline coating. This simplicity makes it possible to avoid the problems of control of the germination and the crystalline growth of the amorphous phase alluded to in the prior patent.

(i) The method according to the invention moreover offers the possibility of varying over a wide range the Ca/P ratio of the nanocrystalline phase and, consequently, its biological properties, particularly its ability to be resorbed more or less rapidly in a biological medium. This variation may be directly obtained by acting on the apatite synthesis conditions, in particular the pH, the sequence of addition of the reagents, the temperature, the presence of foreign ions in the synthesis solution (e.g. carbonate). The apatites directly obtained may thus have a wide range of Ca/P ratios (1.30 to 2) linked to the proportion of $HPO_4^{2-}$ and/or carbonate ions incorporated in the nanocrystalline phase at the time of its synthesis.

(i) Another advantage of the coating method according to the invention stems from the possibility of directly controlling the hydrated layer of the synthesized apatite so as to promote the adhesion of crystals on the substrate, and to control their surface characteristics and the cellular response. These controls are carried out by acting on the maturation time (ageing time of the crystals in solution) and the presence of stabilizers of this hydrated layer, particularly mineral ions such as carbonate, pyrophosphate, $Mg^{2+}$ ions or even organic molecules. These adjuvants may be combined with the synthesis solutions or incorporated in the hydrated layer after the formation of the nanocrystalline apatite.

(iv) Another advantage of the method according to the invention is to benefit of a homogeneous population of nanocrystals, which it is impossible to obtain by the relatively slow hydrolysis method of the amorphous phase according to FR 2 842 750 which leads necessarily to a mixture of crystals of different maturity.

The characteristics and advantages of the method according to the present invention will become clearer in the light of the following examples. These are given purely by way of illustration and should not be interpreted as any limitation to the scope of the method, which extends in particular to means equivalent to those that are disclosed in the present application.

The following figures are also provided to illustrate the present invention:

FIG. 1: Micrograph of a nanocrystalline apatite layer deposited inside the pores of a biphasic HA-TCP ceramic according to the invention.

Figure 2:
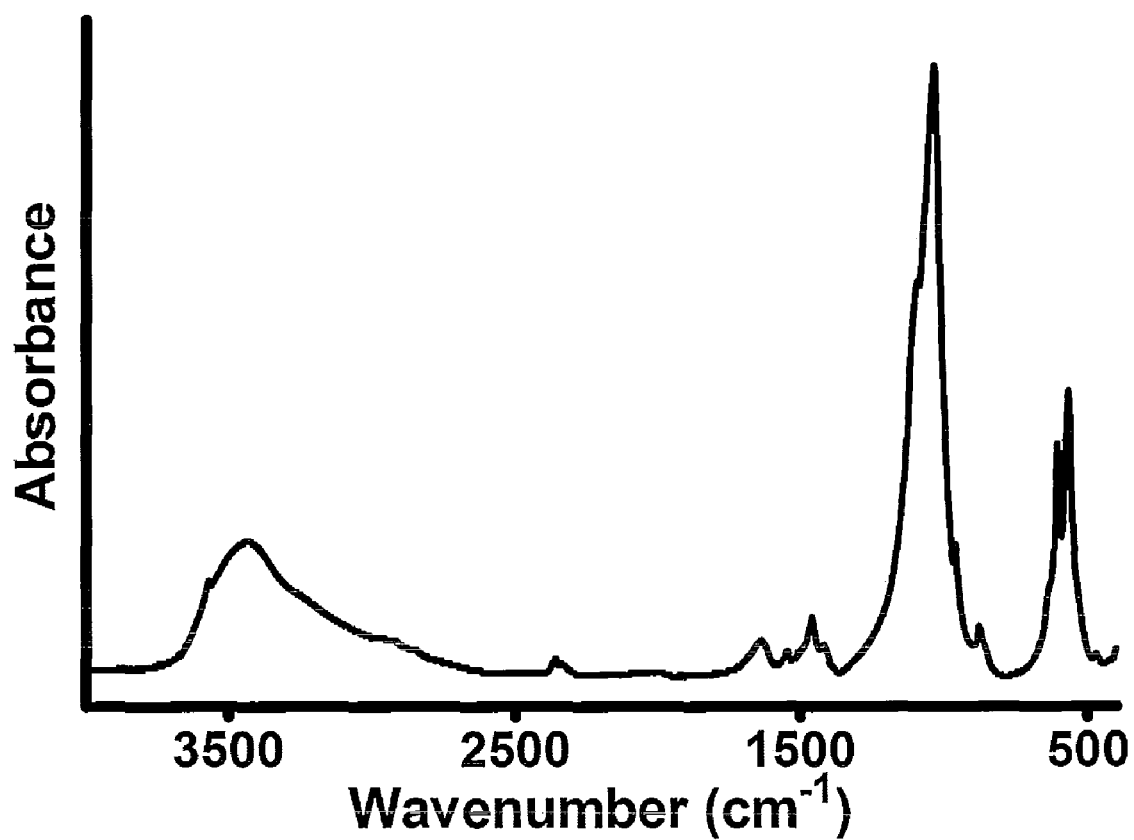
FIG. 2 shows an IR spectrum of nanocrystals deposited in Example 1 of the invention.

FIG. 2: Infrared spectrum of the nanocrystals deposited using the method of example 1 according to the invention.

Figure 3:
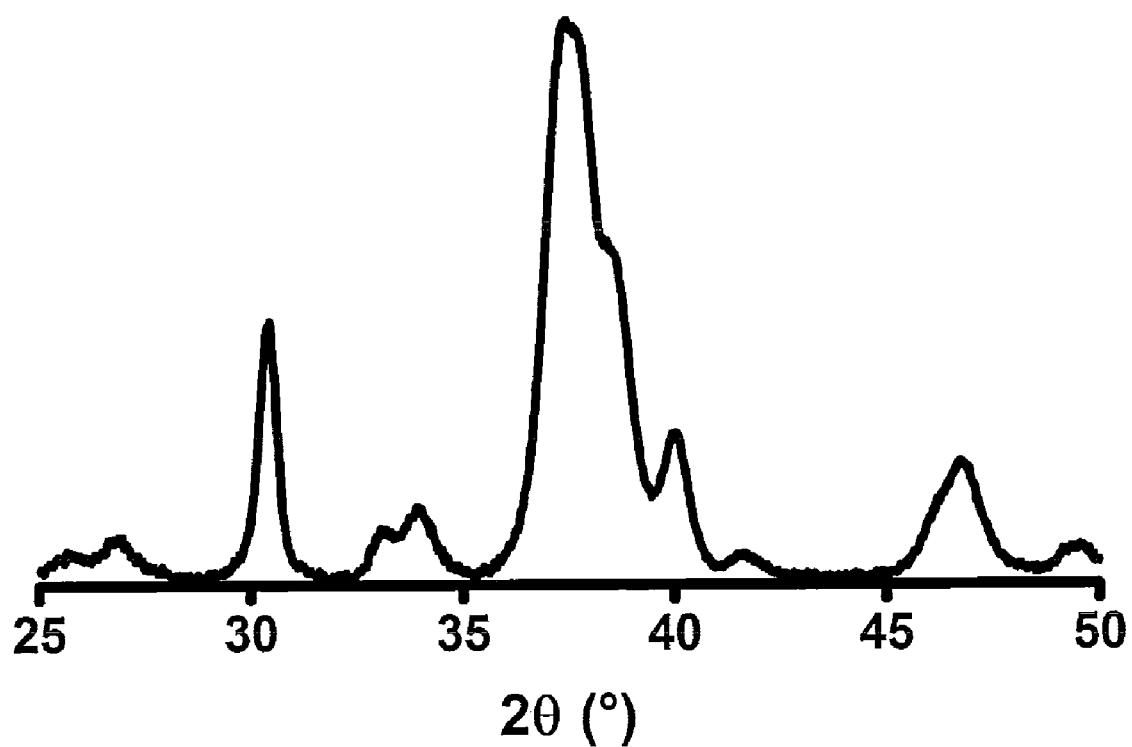
FIG. 3 shows an X-ray diffraction diagram of nanocrystals deposited in Example 1 of the invention.

FIG. 3: X-ray diffraction diagram of the nanocrystals deposited using the method of example 1 according to the invention ($CoK_\alpha$, radiation).

EXAMPLES

Example 1

Deposition of a Nanocrystalline Carbonated Apatite Close to Biological Apatites

Step 1: Synthesis of the carbonated apatite gel

Solution A: 48.8 g $Na_2HPO_4.12H_2O$+18 g $NaHCO_3$ in 400 ml of deionized water.

Solution B: 6.5 g $CaCl_2.2H_2O$ in 150 ml of deionized water.

After complete dissolution of the salts in solutions A and B, pour solution B into solution A. Then filter and thoroughly rinse with deionized water.

Step 2: Add 50 g of gel to 200 ml of water so as to obtain a homogeneous suspension. This suspension will constitute solution C.

Step 3: A porous calcium phosphate ceramic (30 mm³ cube, 70% interconnected porosity) is immersed in solution C arranged in a vacuum flask.

A vacuum is established for around ten minutes while stirring the solution so as to eliminate any bubbles that form. Then, ambient atmospheric pressure is rapidly re-established so as to make the gel penetrate inside the pores of the ceramic. This step is repeated several times if necessary.

Step 4: Drying of the ceramic

The ceramic is introduced in a sealed enclosure in the presence of vaporized ethanol at 60° C. for 24 hours in order to eliminate part of the water contained in the gel and thereby limit the occurrence of cracks upon drying.

The ceramic thus treated is dried in a suitable enclosure at 4° C. for 48 hours.

FIG. 1 illustrates the deposit obtained and the following figures illustrate its main physicochemical characteristics. The chemical analysis gives a Ca/P atomic ratio of 1.50 and a carbonate content of 1.50% by weight. These data are characteristic of a highly lacunar non-stoichiometric apatite.

Phosphate bands characteristic of a phosphocalcic apatite ($v_1 PO_4$: 961 cm$^{-1}$, $v_2 PO_4$: 460 cm$^{-1}$, $v_3 PO_4$: 1030 and 1095 cm$^{-1}$, $v_4 PO_4$: 560 and 600 cm$^{-1}$) may be observed in FIG. 2. The carbonate bands ($v_2 CO_3$, 860-890 cm$^{-1}$ and $v_3 CO_3$: 1400-1550 cm$^{-1}$) show a substitution both of phosphate ions (B-type carbonates) and OH ions (A-type carbonates). The presence of OH ions in low proportion (shoulders at ca. 3570 and 630 cm$^{-1}$) will also be noted.

A diagram characteristic of an apatite may be observed in FIG. 3. No crystallized foreign phase is detected. The crystal dimensions deduced from these diagrams using the Scherrer Formula (length: 24.5±0.5 nm and width-thickness: 10.2±0.3 nm) confirm the nanocrystalline nature of the crystals.

Example 2

Deposition of a Nanocrystalline Non-carbonated Apatite Very Rich in $HPO_4^{2-}$ Ions with a Ca/P Ratio Close to 1.35 and Having a High Proportion of Mineral Ions in the Hydrated Layer Step 1: Synthesis of the apatite gel Solution A: 40 g $(NH_4)_2HPO_4$ in 500 ml of deionized water.

Solution B: 17.4 g $Ca(NO_3)_2.4H_2O$ in 250 ml of deionized water. After complete dissolution of the salts in solutions A and B, pour solution B into solution A. Then filter and thoroughly rinse with deionized water.

Step 2: Add 50 g of gel to 200 ml of water so as to obtain a homogeneous suspension. This suspension will constitute solution C.

Step 3: A porous calcium phosphate ceramic (30 mm³ cube, 70% interconnected porosity) is immersed in solution C arranged in a vacuum flask.

A vacuum is established for approximately ten minutes while stirring the solution so as to eliminate any bubbles that form. Ambient atmospheric pressure is subsequently rapidly re-established so as to make the gel penetrate inside the pores of the ceramic. This step is repeated several times if necessary.

Step 4: Drying of the ceramic

The ceramic is dried in air then under vacuum at room temperature.

The atomic Ca/P ratio for this deposit is close to 1.35 and its $HPO_4^{2-}$ ion content is close to 29%. The size of the crystals is: length: 17 nm, width-thickness: 5 nm.

Example 3

Deposition of a Nanocrystalline Carbonated Apatite with a Ca/P Ratio Close to 1.6

Step 1: Synthesis of the carbonated apatite gel

Solution A: 48.8 g $Na_2HPO_4.12H_2O$+18 g $NaHCO_3$ in 400 ml of deionized water.

Solution B: 6.5 g $CaCl_2.2H_2O$ in 150 ml of deionized water.

After complete dissolution of the salts in solutions A and B, pour solution B into solution A. The suspension is left to mature for several months. Subsequently filter and thoroughly rinse with deionized water.

The other steps are identical to those of example 1.

The Ca/P ratio for these deposits (2 months' maturation) is 1.58; C/P ratio: 0.14. Crystal length: 25 nm.

Example 4

Deposition of a Strontium-doped Nanocrystalline Carbonated Apatite

Step 1: Synthesis of the carbonated apatite gel

Solution A: 40 g $(NH_4)_2HPO_4$+20 g $NaHCO_3$ in 500 ml of deionized water.

Solution B: 17.7 g $CaNO_3$ in 250 ml of deionized water. After complete dissolution of the salts in solutions A and B, pour solution B into solution A. Then filter and thoroughly rinse with deionized water.

Step 2: Add 100 g of gel to 200 ml of a strontium nitrate solution (0.5 M) for 10 minutes under agitation then filter and thoroughly rinse with deionized water.

Step 3: Add 100 g of gel to 400 ml of water so as to obtain a homogeneous suspension. This suspension will constitute solution C.

Step 4: A porous calcium phosphate ceramic (1 cm³ cube, 80% interconnected porosity) is immersed in solution C arranged in a vacuum flask.

A vacuum is established for ca. ten minutes while stirring the solution so as to eliminate any bubbles that form. Ambient atmospheric pressure is subsequently rapidly re-established so as to make the gel penetrate inside the pores of the ceramic. This step is repeated several times if necessary.

Step 5: The ceramic thus treated is dried in the oven at 50° C. for 48 hours.

The substitution rates of calcium by strontium can range from 0 to 20% depending on the concentration of exchange solutions and the maturation state of the apatite.

Example 5

Deposition of a Nanocrystalline Carbonated Apatite Associating a Growth Factor

Steps 1-5 of example 1 are unchanged. The coated ceramic is then immersed in a solution of rhBMP-2 growth factor. The factor then fixes on the activated ceramic in considerably higher proportion than on the non-activated ceramic (517 µg/g instead of 397 µg/g).

What is claimed is:

1. Porous biomaterials surface activation method wherein it comprises the following steps:
   a) preparing a nanocrystalline apatitic calcium phosphate analogous to bone mineral by mixing a calcium salt solution with a phosphate salt solution in a Ca/P ratio ranging between 1.3 and 2 at a temperature ranging between 0 and 60 ° C.,
   b) slurrying the mixture obtained in step a) in an aqueous solution so as to obtain an aqueous suspension comprising a fluid, homogeneous paste containing 80 to 98% of water,
   c) contacting a porous biomaterial with the suspension obtained in step b),
   d) drying the porous biomaterial at a temperature below 100 ° C.

2. Method according to claim 1, wherein the mixture obtained once step a) is completed undergoes a treatment to modify the surface of the nanocrystals by bringing it into contact with at least one compound exhibiting a biological activity and/or modifying the surface properties of the nanocrystals, said compound being selected from the group consisting of a mineral ion, an organic molecule, and mixture thereof.

3. Method according to claim 1, wherein the biomaterial obtained once step d) is completed undergoes a surface treatment by bringing it into contact with at least one compound exhibiting a biological activity and/or modifying the surface properties of the nanocrystals, said compound being selected from the group consisting of a mineral ion, an organic molecule, and mixture thereof.

4. Method according to claim 2, wherein the surface treatment is carried out by ion exchange with an aqueous solution containing at least one ion selected from the group consisting of $Mg^{2+}$, $Sr^{2+}$, $Mn^{2+}$, $SiO_4^{4-}$, $VO_4^{3-}$, and mixtures thereof.

5. Method according to claim 2, wherein the surface treatment is carried out by adsorption of at least one organic molecule selected from the group consisting of growth factors, antibiotics, and mixtures thereof.

6. Method according to claim 1, wherein the mixture obtained once step a) is completed has a Ca/P ratio ranging between 1.33 and 1.67.

7. Method according to claim 1, wherein prior to step c), the biomaterial is cleared of any organic impurity that could hinder wetting by the aqueous suspension by prior heating in air at a temperature of about 900 ° C. for 3 to 5 minutes, or by ozonization treatment.

8. Method according to claim 1, wherein step c) is carried out by immersion of the biomaterial in the solution obtained in step b) or by spraying or coating the solution obtained in step b) on the biomaterial.

9. Method according to claim 8, wherein step c) is carried out under partial vacuum with a pressure ranging between 10 to 30 mm Hg.

10. Method according to claim 1, wherein, prior to step d), the biomaterial obtained at the end of step c) is partially and progressively dehydrated.

11. Method according to claim 1, wherein steps b), c) and d) are repeated.

12. Method according to claim 1, wherein the biomaterial is a phosphocalcic ceramic.

13. Method according to claim 2, wherein the biomaterial obtained once step d) is completed undergoes a surface treatment by bringing it into contact with at least one compound exhibiting a biological activity and/or modifying the surface properties of the nanocrystals, said compound being selected from the group consisting of a mineral ion, an organic molecule, and mixture thereof.

14. Method according to claim 3, wherein the surface treatment is carried out by ion exchange with an aqueous solution containing at least one ion selected from the group consisting of $Mg^{2+}$, $Sr^{2+}$, $Mn^{2+}$, $SiO_4^{4-}$, $VO_4^{3-}$, and mixtures thereof.

15. Method according to claim 3, wherein the surface treatment is carried out by adsorption of at least one organic molecule selected from the group consisting of growth factors, antibiotics, and mixtures thereof.

16. Method according to claim 4, wherein the surface treatment is carried out by adsorption of at least one organic molecule selected from the group consisting of growth factors, antibiotics, and mixtures thereof.

17. Method according to claim 2, wherein the mixture obtained once step a) is completed has a Ca/P ratio ranging between 1.33 and 1.67.

18. Method according to claim 3, wherein the mixture obtained once step a) is completed has a Ca/P ratio ranging between 1.33 and 1.67.

19. Method according to claim 4, wherein the mixture obtained once step a) is completed has a Ca/P ratio ranging between 1.33 and 1.67.

20. Method according to claim 5, wherein the mixture obtained once step a) is completed has a Ca/P ratio ranging between 1.33 and 1.67.

21. Method according to claim 2, wherein prior to step c), the biomaterial is cleared of any organic impurity that could hinder wetting by the aqueous suspension by prior heating in air at a temperature of about 900 ° C. for 3 to 5 minutes, or by ozonization treatment.

* * * * *